US011944472B2

(12) United States Patent
Morita

(10) Patent No.: US 11,944,472 B2
(45) Date of Patent: Apr. 2, 2024

(54) RADIOGRAPHIC SYSTEM, RADIOGRAPHIC APPARATUS, INFORMATION PROCESSING APPARATUS, AND INFORMATION PROCESSING METHOD

(71) Applicant: FUJIFILM CORPORATION, Tokyo (JP)

(72) Inventor: Junya Morita, Kanagawa (JP)

(73) Assignee: FUJIFILM CORPORATION, Tokyo (JP)

( * ) Notice: Subject to any disclaimer, the term of this patent is extended or adjusted under 35 U.S.C. 154(b) by 288 days.

(21) Appl. No.: 17/645,748

(22) Filed: Dec. 23, 2021

(65) Prior Publication Data
US 2022/0240874 A1 Aug. 4, 2022

(30) Foreign Application Priority Data

Feb. 4, 2021 (JP) .................................. 2021-016788

(51) Int. Cl.
*A61B 6/04* (2006.01)
*A61B 6/08* (2006.01)
*A61B 6/50* (2024.01)

(52) U.S. Cl.
CPC .......... *A61B 6/0492* (2013.01); *A61B 6/0414* (2013.01); *A61B 6/08* (2013.01); *A61B 6/502* (2013.01)

(58) Field of Classification Search
CPC ....... A61B 6/0492; A61B 6/0414; A61B 6/08; A61B 6/502
See application file for complete search history.

(56) References Cited

U.S. PATENT DOCUMENTS

2014/0328458 A1* 11/2014 Erhard ................ A61B 6/0414
702/19
2015/0265186 A1    9/2015 Kuwabara
2017/0367671 A1   12/2017 Arai et al.
2018/0046875 A1*   2/2018 Caluser ................ A61B 6/584

FOREIGN PATENT DOCUMENTS

JP    2015-177884 A    10/2015
JP    2017-225634 A    12/2017

* cited by examiner

*Primary Examiner* — David P Porta
*Assistant Examiner* — Mamadou Faye
(74) *Attorney, Agent, or Firm* — SOLARIS Intellectual Property Group, PLLC

(57) ABSTRACT

The radiographic system includes an exposure table on which a breast of a subject is placed, a compression plate that compresses the breast placed on the exposure table, a marker having a two-dimensional pattern provided on the compression plate, a radiation source that irradiates the compressed breast with radiation, a camera that captures a visible light image including the marker, and a processor that derives height information of the compression plate with respect to the exposure table based on a marker image showing the marker reflected in the visible light image.

14 Claims, 13 Drawing Sheets

RADIOGRAPHIC SYSTEM, RADIOGRAPHIC APPARATUS, INFORMATION PROCESSING APPARATUS, AND INFORMATION PROCESSING METHOD

CROSS-REFERENCE TO RELATED APPLICATIONS

The present application claims priority under 35 U.S.C. § 119 to Japanese Patent Application No. 2021-016788 filed on Feb. 4, 2021. The above application is hereby expressly incorporated by reference, in its entirety, into the present application.

BACKGROUND

1. Technical Field

The technique of the present disclosure relates to a radiographic system, a radiographic apparatus, an information processing apparatus, and an information processing method.

2. Description of the Related Art

A mammography apparatus that images a breast of a subject using radiation is known. The mammography apparatus is provided with a compression plate configured to be movable in a direction coming close to and separating from an exposure table having a built-in radiation detector. In mammography imaging, in order to flatten and fix the breast of the subject, the breast is interposed between the exposure table and the compression plate and is compressed. Flattening and compressing the breast reduces overlapping of mammary glands and makes it easier to find a lesion. In addition, thinning the breast makes it possible to reduce the radiation dose required for imaging.

In mammography imaging, the thickness of the compressed breast, that is, the height of the compression plate with respect to the exposure table, is important information for determining imaging conditions and various image conditions. Various methods are known as a method for measuring the thickness of the compressed breast. For example, JP2015-177884A discloses that a marker for absorbing radiation is provided on a compression plate, and the height of the compression plate is measured based on a marker image reflected in a radiation image. In addition, JP2017-225634A discloses that the height of a compression plate is measured by acquiring an image of a side surface of the breast in a state of being compressed by the compression plate with an optical camera.

SUMMARY

However, in the technique disclosed in JP2015-177884A, since the marker image is reflected in the radiation image, the breast image and the marker image may overlap each other. In this way, in a case where the breast image and the marker image overlap each other, the marker image interferes with the diagnosis of the breast. In order to prevent the breast image and the marker image from overlapping each other, the marker has to be disposed at an end part of the compression plate. Therefore, in the technique disclosed in JP2015-177884A, the height of the end part of the compression plate is measured.

In the technique disclosed in JP2017-225634A, since the height of the compression plate is measured based on the image of the side surface of the breast, the measured height is the height of an end part of the compression plate, as in the technique disclosed in JP2015-177884A.

The compression plate may be inclined or deflected. In a case where the compression plate is inclined or deflected, the thickness of the breast cannot be accurately measured. Since the techniques disclosed in JP2015-177884A and JP2017-225634A both measure the height of the end part of the compression plate, the thickness of the breast cannot be accurately measured in consideration of the influence of the inclination or deflection of the compression plate.

An object of the technique of the present disclosure is to provide a radiographic system, a radiographic apparatus, an information processing apparatus, and an information processing method capable of accurately measuring the thickness of a breast in consideration of the influence of the inclination or deflection of a compression plate.

In order to achieve the above object, the radiographic system of the present disclosure comprises: an exposure table on which a breast of a subject is placed; a compression plate that compresses the breast placed on the exposure table; a marker having a two-dimensional pattern provided on the compression plate; a radiation source that irradiates the compressed breast with radiation; a camera that captures a visible light image including the marker; and a height information derivation unit that derives height information of the compression plate with respect to the exposure table based on a marker image showing the marker reflected in the visible light image.

It is preferable that the height information derivation unit derives the height information based on a rate of change in a length of the marker image according to a height of the compression plate.

It is preferable that in a case where a distance from the camera to the exposure table is S, and a length of the marker image in one direction in a case where the height of the compression plate with respect to the exposure table is H is $L(H)$, the height information derivation unit derives the height information based on a relational expression of $H = S \times (1 - L(0)/L(H))$.

It is preferable that the height information includes a height of the compression plate at a plurality of positions.

It is preferable that the two-dimensional pattern is any one of a frame shape, a lattice shape, a dot shape, a cross shape, or a combination thereof.

It is preferable that the marker has a color different from a color of the compression plate.

It is preferable that the marker is formed by attaching a member to the compression plate.

It is preferable that the marker has a radiation-transmitting property.

It is preferable that at least a part of the marker is disposed at a position overlapping the breast.

It is preferable that the camera is provided in a holding part that holds the radiation source.

It is preferable that the exposure table, the compression plate, the marker, and the camera are provided in a radiographic apparatus, and that the height information derivation unit is provided in an information processing apparatus connected to the radiographic apparatus.

A radiographic apparatus of the present disclosure comprises: an exposure table on which a breast of a subject is placed; a compression plate that compresses the breast placed on the exposure table; a marker having a two-dimensional pattern provided on the compression plate; a radiation source that irradiates the compressed breast with radiation; and a camera that captures a visible light image including the marker.

An information processing apparatus of the present disclosure is an information processing apparatus that is connected to a radiographic apparatus including an exposure table on which a breast of a subject is placed, a compression plate that compresses the breast placed on the exposure table, a marker having a two-dimensional pattern provided on the compression plate, a radiation source that irradiates the compressed breast with radiation, and a camera that captures a visible light image including the marker, the information processing apparatus comprising: a processor, in which the processor derives height information of the compression plate with respect to the exposure table based on a marker image showing the marker reflected in the visible light image.

An information processing method of the present disclosure is an information processing method of a radiographic apparatus including an exposure table on which a breast of a subject is placed, a compression plate that compresses the breast placed on the exposure table, a marker having a two-dimensional pattern provided on the compression plate, a radiation source that irradiates the compressed breast with radiation, and a camera that captures a visible light image including the marker, the information processing method comprising: deriving height information of the compression plate with respect to the exposure table based on a marker image showing the marker reflected in the visible light image.

According to the technique of the present disclosure, it is possible to provide a radiographic system, a radiographic apparatus, an information processing apparatus, and an information processing method capable of accurately measuring the thickness of a breast in consideration of the influence of the inclination or deflection of a compression plate.

BRIEF DESCRIPTION OF THE DRAWINGS

Exemplary embodiments according to the technique of the present disclosure will be described in detail based on the following figures, wherein.

DETAILED DESCRIPTION

Hereinafter, embodiments according to the technique of the present disclosure will be described with reference to the drawings.

Figure 1:
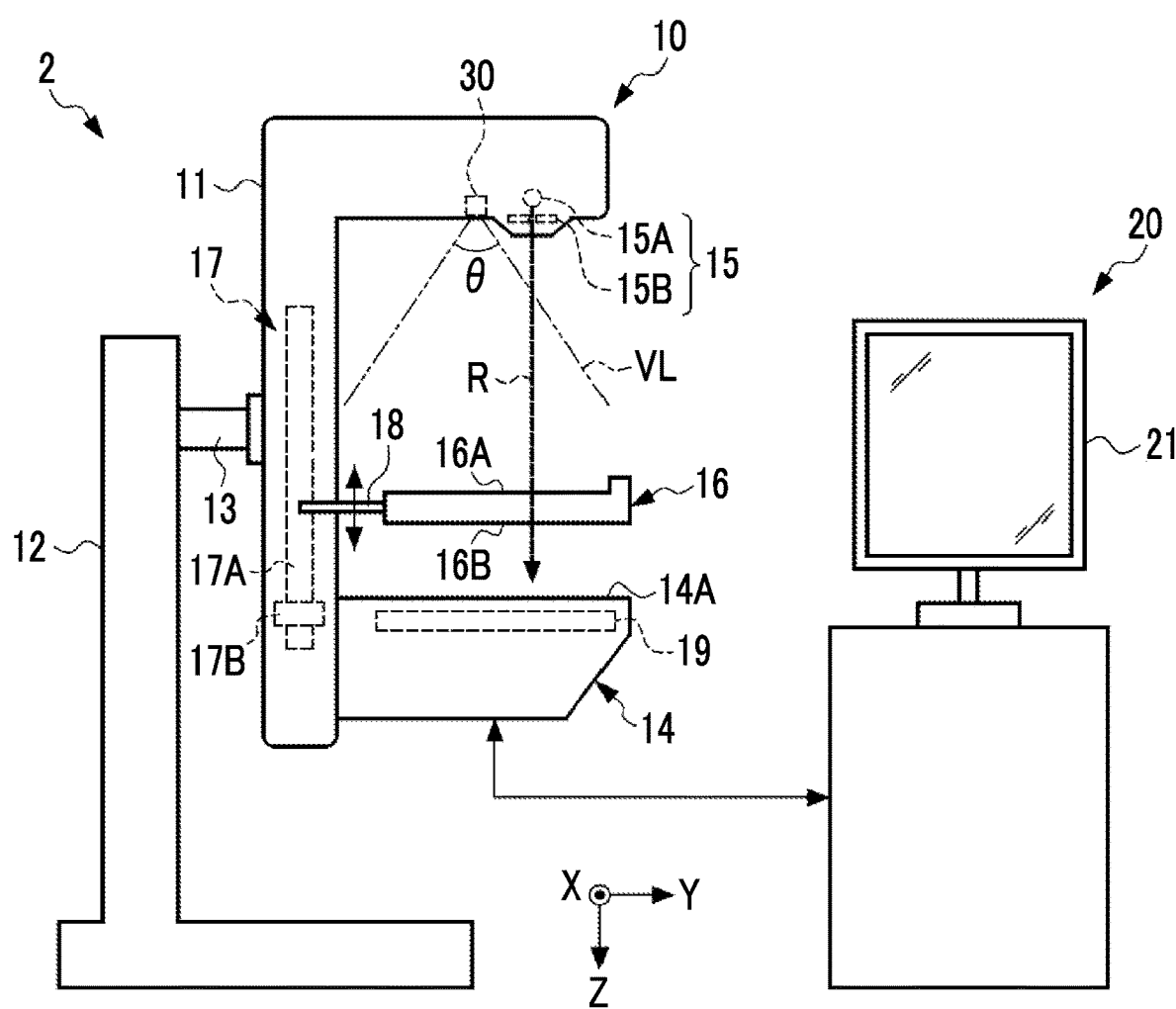
FIG. 1 is a schematic view showing an example of a configuration of a radiographic system.

First, a configuration of a radiographic system according to an embodiment will be described. FIG. 1 shows a configuration of a radiographic system 2 of the present embodiment.

As shown in FIG. 1, the radiographic system 2 has a function of capturing a radiation image via an operation of a user such as a doctor or a radiological technician based on information (for example, an imaging menu) input from an external system (for example, a radiology information system (RIS)) via a console 20.

The radiographic system 2 includes a mammography apparatus 10 and a console 20. The mammography apparatus 10 is an example of a "radiographic apparatus" according to the technique of the present disclosure. The console 20 is an example of an "information processing apparatus" according to the disclosed technique.

The mammography apparatus 10 is a radiographic apparatus that performs radiography on a breast of a subject as an imaging target. The mammography apparatus 10 may be an apparatus that images the breast of the subject not only in a state in which the subject stands up but also in a sitting state in which the subject sits on a chair or the like, or need only be a radiographic apparatus capable of at least separately imaging the right and left breasts of the subject.

The mammography apparatus 10 comprises an arm part 11 and a base 12. The arm part 11 is connected to the base 12 via a shaft part 13. The arm part 11 is held by the base 12 so as to be movable in a vertical direction (Z-axis direction). In addition, the arm part 11 is attached to the base 12 so as to be rotatable about the shaft part 13 as a rotation axis. The arm part 11 is an example of a "holding part that holds a radiation source" according to the technique of the present disclosure.

An exposure table 14 is provided on a lower part of the arm part 11. In addition, a radiation source 15 is provided on an upper part of the arm part 11. The radiation source 15 is disposed at a position corresponding to an exposure surface 14A of the exposure table 14. The exposure surface 14A is a plane including an X-axis direction and a Y-axis direction orthogonal to the Z-axis direction. The breast of the subject is placed on the exposure surface 14A.

A compression plate 16 is attached to the arm part 11 so as to be movable in the Z-axis direction. The compression plate 16 is movable in a direction coming close to and separating from the exposure table 14. That is, the height of the compression plate 16 with respect to the exposure surface 14A is variable. The compression plate 16 is a plate-shaped compression member, and has an upper surface 16A and a lower surface 16B parallel to the exposure surface 14A. The compression plate 16 presses the breast placed on the exposure surface 14A downward with the lower surface 16B, thereby compressing the breast.

A moving mechanism 17 for moving the compression plate 16 is provided inside the arm part 11. The moving mechanism 17 is a linear actuator including a ball screw 17A and a motor 17B. The compression plate 16 is connected to the ball screw 17A via a support portion 18. The compression plate 16 slides between the exposure table 14 and the radiation source 15 in a case where the motor 17B is driven.

The compression plate 16 is formed of a material that transmits radiation R emitted by the radiation source 15. The compression plate 16 of the present embodiment is formed of, for example, a thermoplastic plastic (for example, polyethylene terephthalate) which is a resin material. The material for forming the compression plate 16 is not limited to this, and polycarbonate, acrylic, polypropylene, or the like can be used. In addition, the compression plate 16 is preferably formed of a transparent material that transmits visible light.

The compression plate 16 is not limited to a form of compressing the entire breast, and may be a form of compressing a part of the breast. That is, the compression plate 16 may be smaller than the breast. In addition, the compression plate 16 may be a compression plate having a concave cross-sectional shape in which a bottom portion contacting the breast is surrounded by a wall portion. In the present disclosure, the compression plate 16 is referred to as a "compression plate" for convenience, but the compression plate 16 is not limited to one formed of a plate-shaped member, and may be, for example, one formed of a film-shaped member.

The radiation source 15 includes a radiation tube 15A that emits the radiation R and a collimator 15B that limits an irradiation field of the radiation R. The radiation source 15 irradiates the breast compressed by the compression plate 16 with the radiation R. The radiation R is, for example, an X-ray.

A radiation detector 19 is provided inside the exposure table 14. The radiation detector 19 is disposed such that a detection surface for detecting the radiation R is parallel to the exposure surface 14A.

The radiation detector 19 detects the radiation R emitted from the radiation source 15 and transmitted through the compression plate 16 and the breast. The radiation detector 19 is a so-called flat panel detector. The radiation detector 19 has radiation detection pixels arranged two-dimensionally, and generates a radiation image by detecting the dose of the radiation R incident on each radiation detection pixel.

The radiation detector 19 is, for example, an indirect conversion type radiation detector that converts the radiation R into visible light and that converts the converted visible light into electric charge. The radiation detector 19 may be a direct conversion type radiation detector that directly converts the radiation R into electric charge.

A camera 30 for capturing a visible light image is provided on an upper part of the arm part 11. The camera 30 receives visible light VL and generates a visible light image based on the received visible light VL. The camera 30 is provided, for example, in the vicinity of the radiation source 15. The camera 30 has an angle of view θ set so as to image a region including the upper surface 16A of the compression plate 16. As will be described in detail below, a marker having a two-dimensional pattern is provided on the upper surface 16A of the compression plate 16, and the camera 30 images at least a region including the marker. The visible light image generated by the camera 30 is used in the console 20 for deriving the height information of the compression plate 16 with respect to the exposure table 14.

In the present embodiment, the radiation image generated by the radiation detector 19 of the mammography apparatus 10 and the visible light image generated by the camera 30 are transmitted to the console 20. The console 20 has a control function of controlling the operation of the mammography apparatus 10. The console 20 controls the mammography apparatus 10 by using an imaging menu or various kinds of information acquired from an external system or the like via a wireless communication local area network (LAN) or the like.

The console 20 is composed of a computer. The console 20 has a display unit 21 that displays various kinds of information. The display unit 21 is a display device such as a liquid crystal display or an organic electro luminescence (EL) display.

Figure 2:
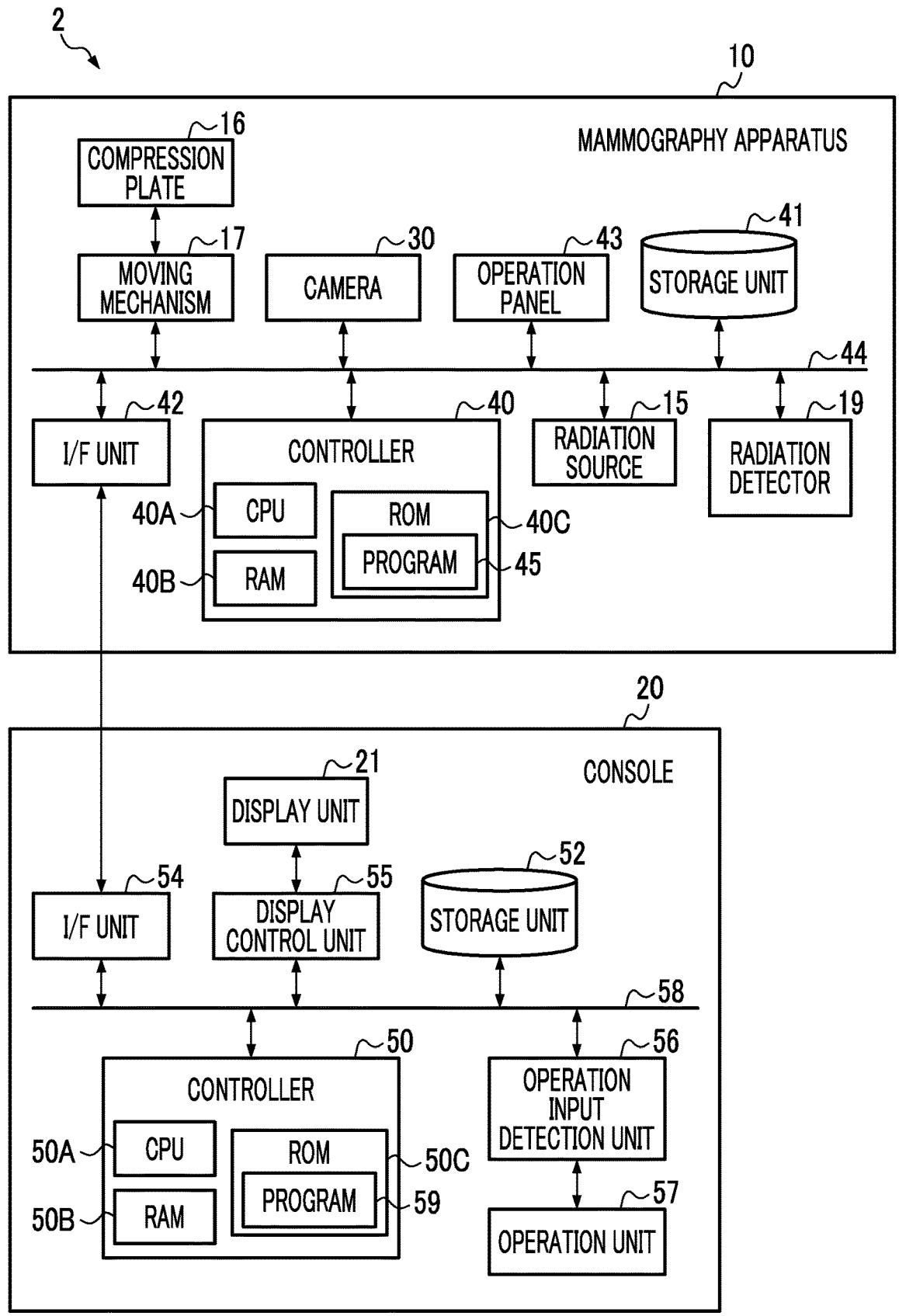
FIG. 2 is a block diagram showing an example of a hardware configuration of the radiographic system.

FIG. 2 shows an example of a hardware configuration of the radiographic system 2. The mammography apparatus 10 comprises the radiation source 15, the compression plate 16, the moving mechanism 17, the radiation detector 19, a controller 40, a storage unit 41, an interface (I/F) unit 42, and an operation panel 43. The radiation source 15, the moving mechanism 17, the radiation detector 19, the controller 40, the storage unit 41, the I/F unit 42, and the operation panel 43 are connected to each other via a bus 44 so as to exchange various kinds of information.

The controller 40 is composed of, for example, a central processing unit (CPU) 40A, a random access memory (RAM) 40B, and a read only memory (ROM) 40C. Various kinds of data including a program 45 executed by the CPU 40A are stored in the ROM 40C in advance. The RAM 40B has a function of temporarily storing various kinds of data.

The storage unit 41 is composed of a hard disk drive (HDD), a solid state drive (SSD), or the like. The storage unit 41 stores the radiation image generated by the radiation detector 19 and the visible light image generated by the camera 30.

The I/F unit 42 has a function of performing communication of various kinds of information with the console 20 through wireless communication or wired communication.

The operation panel 43 is composed of, for example, a touch panel display, receives information input by the user, and displays the information. The user can confirm the imaging conditions and give an imaging start instruction via the operation panel 43. The controller 40 performs various kinds of control of the mammography apparatus 10 based on the instruction input via the operation panel 43.

The console 20 comprises a controller 50, a storage unit 52, an I/F unit 54, a display control unit 55, a display unit 21, an operation input detection unit 56, and an operation unit 57. The controller 50, the storage unit 52, the I/F unit 54, the display control unit 55, and the operation input detection unit 56 are connected to each other via a bus 58 so as to exchange various kinds of information.

The controller 50 is composed of, for example, a CPU 50A, a RAM 50B, and a ROM 50C. Various kinds of data including a program 59 executed by the CPU 50A are stored in the ROM 50C in advance. The RAM 50B has a function of temporarily storing various kinds of data.

The I/F unit 54 has a function of performing communication of various kinds of information with the mammography apparatus 10 and an external device (not shown)

through wireless communication or wired communication. The external device is, for example, a radiology information system (RIS).

The display control unit 55 has a function of controlling the display of various kinds of information on the display unit 21 described above.

The operation unit 57 is composed of a keyboard, a mouse, a touch panel, a touch pen, or the like. The operation unit 57 is used in a case where the user inputs an instruction or various kinds of information relating to the capturing of a radiation image. In a case where the operation unit 57 is a touch panel, the operation unit 57 can be integrated with the display unit 21. The operation input detection unit 56 has a function of detecting the operation of the user on the operation unit 57.

Figure 3:
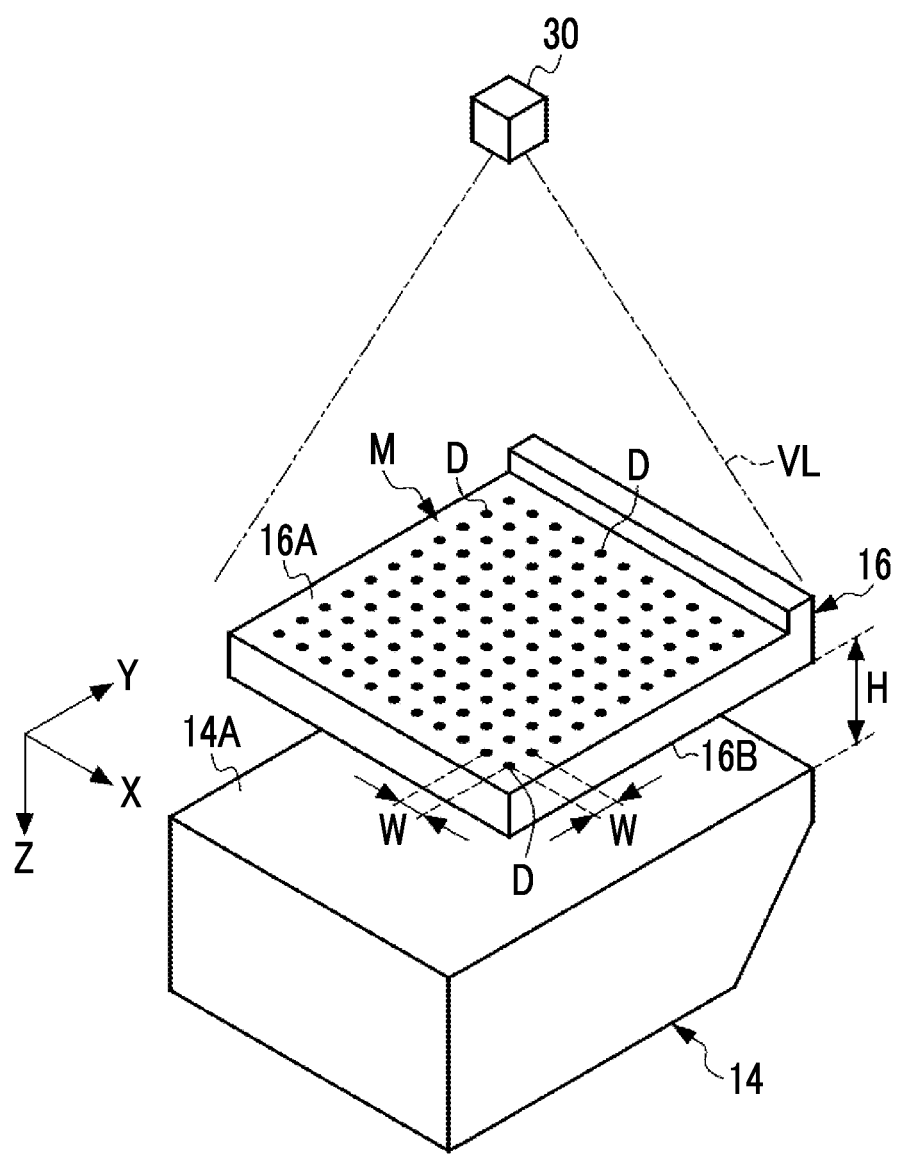
FIG. 3 is a perspective view showing an example of a marker provided on a compression plate.

FIG. 3 shows an example of a marker M having a two-dimensional pattern provided on the compression plate 16. The marker M shown in FIG. 3 is formed by applying ink to the upper surface 16A of the compression plate 16 via a method such as screen printing. The marker M is not limited to print formation, and may be formed by attaching a member such as a colored resin film to the upper surface 16A.

In the present example, the marker M is composed of a plurality of dots D arranged in a two-dimensional lattice shape. The dots D are arranged at equal intervals in the X-axis direction and the Y-axis direction. An interval between the dots D in the X-axis direction and an interval between the dots D in the Y-axis direction are denoted by W.

The marker M has a color different from that of the compression plate 16. For example, the compression plate 16 is transparent and the marker M is black. The colors of the marker M and the compression plate 16 are not limited to this, and may be other colors.

In addition, in the present example, at least a part of the marker M is disposed at a position overlapping the breast placed on the exposure table 14. In a case where the marker M has radiation absorbency, a marker image is reflected in the radiation image generated by the radiation detector 19, thereby causing a problem in the diagnosis of the breast. Therefore, in the present example, the marker M is formed of a material having a radiation-transmitting property so as not to be reflected in the radiation image. A radiation transmittance of the marker M is not limited to 100% and may be less than 100%. The radiation transmittance of the marker M need only be such that the marker M is not visible in the radiation image. In addition, the radiation transmittance of the marker M need only be substantially the same as a radiation transmittance of the compression plate 16. In a case where the radiation transmittance of the marker M is substantially the same as that of the compression plate 16, the image of the marker M is not visible in the radiation image even though the radiation transmittance is less than 100%.

The camera 30 generates a visible light image by imaging the upper surface 16A on which the marker M is formed from above the compression plate 16. The size of the image of the marker M reflected in the visible light image changes according to a height H of the compression plate 16 with respect to the exposure table 14.

Figure 4A:
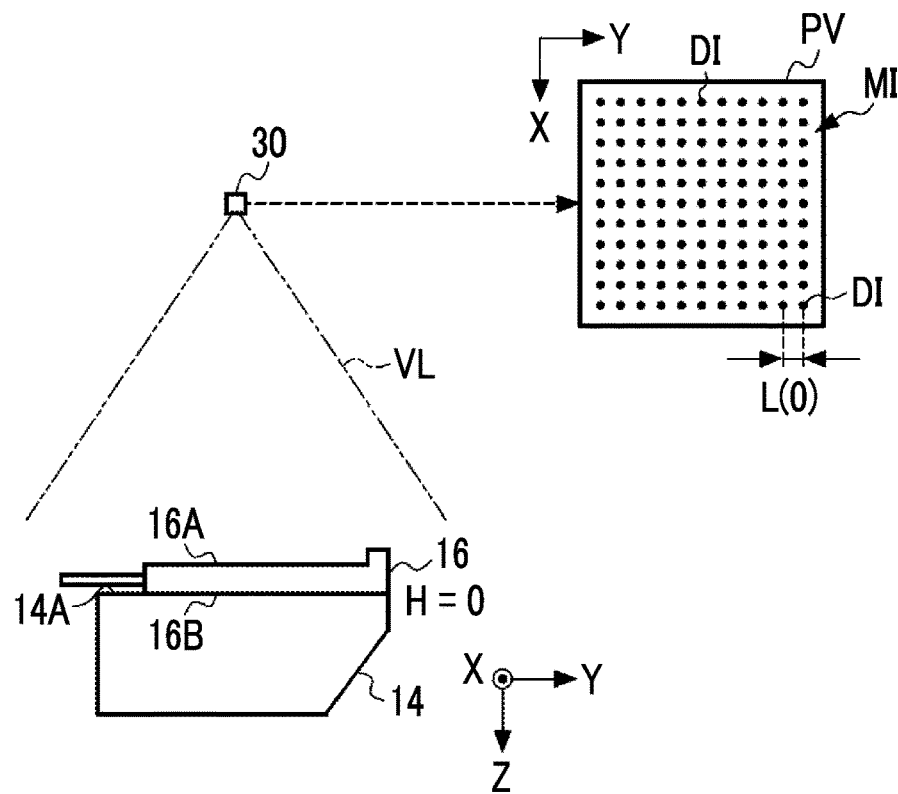
FIGS. 4A and 4B are diagrams showing an example of a change in a visible light image according to the height of the compression plate.
Figure 4B:
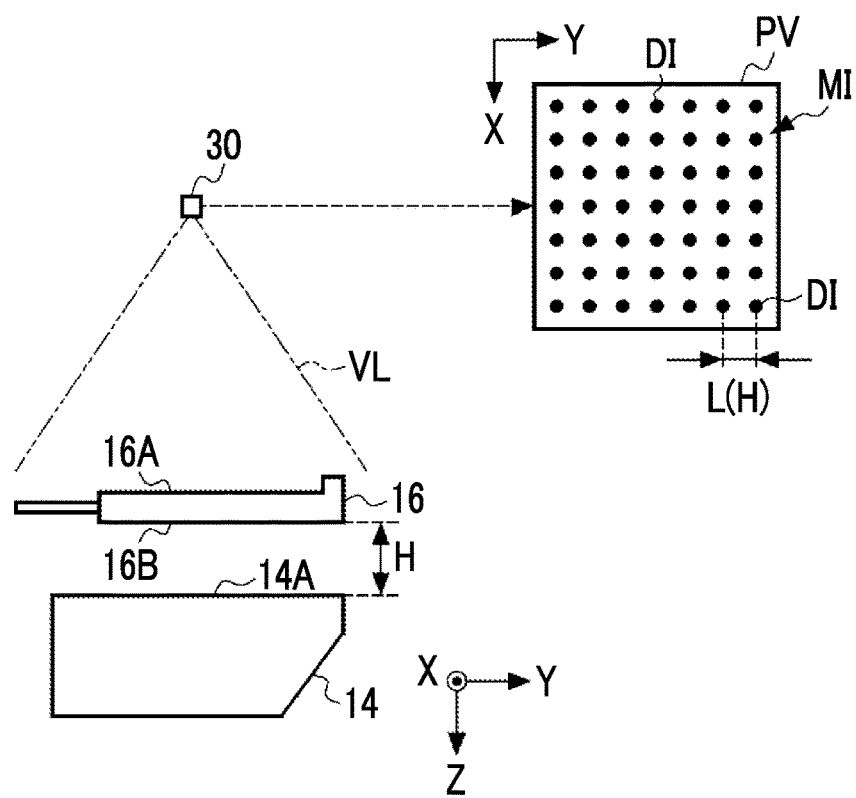

FIGS. 4A and 4B show the change in the visible light image according to the height H of the compression plate 16. FIG. 4A shows an example of a visible light image PV captured by the camera 30 in a case where H=0. In the case of H=0, an interval between the compression plate 16 and the exposure table 14 is set to 0 by bringing the lower surface 16B of the compression plate 16 into contact with the exposure surface 14A of the exposure table 14. In this case, an interval between images DI of the dots D (hereinafter, referred to as a dot image) included in an image MI of the marker M (hereinafter, referred to as a marker image) reflected in the visible light image PV is denoted by L(0). The interval L(0) has the same value in the X-axis direction and the Y-axis direction.

FIG. 4B shows an example of a visible light image PV captured by the camera 30 in a case where H>0. In the case of H>0, an interval between the compression plate 16 and the exposure table 14 is made greater than 0 by separating the lower surface 16B of the compression plate 16 from the exposure surface 14A of the exposure table 14. In this case, an interval between dot images DI included in a marker image MI reflected in the visible light image PV is denoted by L(H). In a case where the compression plate 16 is flat and is parallel to the exposure surface 14A of the exposure table 14, that is, in a case where the compression plate 16 is not inclined or deflected, the interval L(H) between the two adjacent dot images DI has a constant value in the X-axis direction and the Y-axis direction. The interval L(H) between the dot images DI is an example of a "length of the marker image in one direction" according to the technique of the present disclosure.

In a case where H>0, the position of the marker M is closer to the camera 30 than in a case where H=0, so that the marker image MI reflected in the visible light image PV is enlarged. Therefore, the interval L(H) is larger than the interval L(0). As will be described in detail below, since the ratio of the interval L(H) to the interval L(0) depends on the height H of the compression plate 16, the height H can be derived based on the interval L(0) and the interval L(H).

Figure 5:
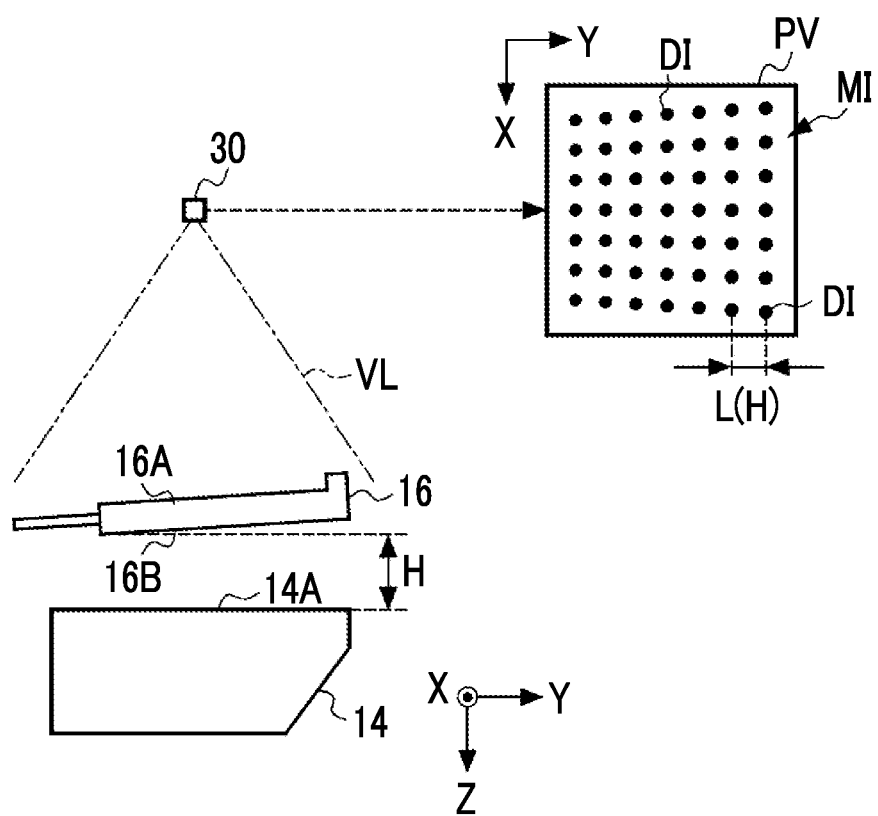
FIG. 5 is a diagram showing an example of a change in the visible light image in a case where the compression plate is inclined.

FIG. 5 shows an example of the visible light image PV captured by the camera 30 in a case where the compression plate 16 is inclined. As shown in FIG. 5, in a case where the compression plate 16 is inclined, the interval L(H) between the dot images DI included in the marker image MI reflected in the visible light image PV changes. In the present example, the interval L(H) changes according to the position in the Y-axis direction. A two-dimensional distribution of the height H of the compression plate 16 can be derived by obtaining the interval L(H) between each of the dot images DI included in the marker image MI and the adjacent dot image DI. In a case where the compression plate 16 is deflected, the two-dimensional distribution of the height H of the compression plate 16 can be derived by the same method. Hereinafter, the two-dimensional distribution of the height H of the compression plate 16 is referred to as height information HI. The height information HI includes the height H of the compression plate 16 at a plurality of positions.

Figure 6:
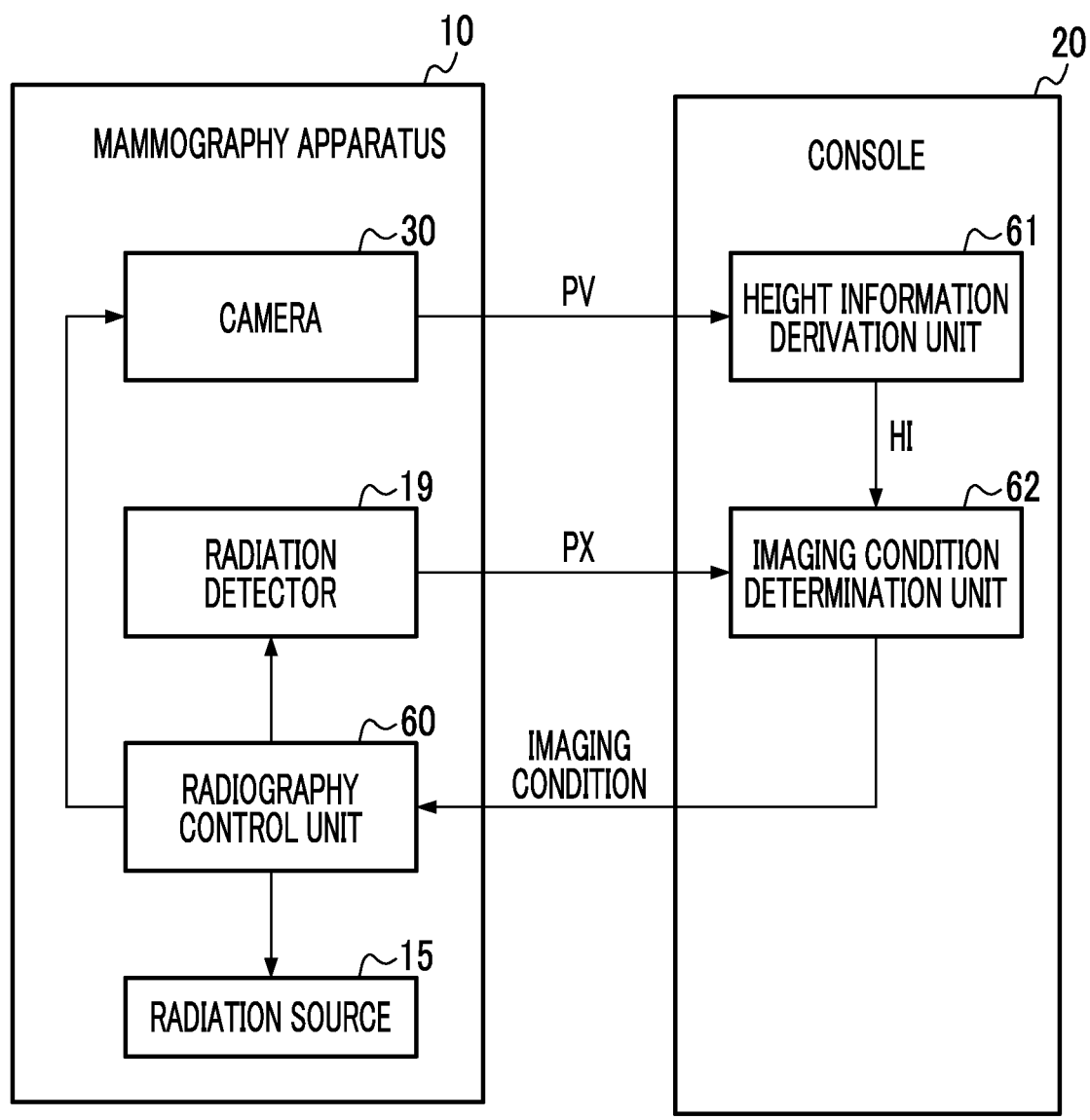
FIG. 6 is a block diagram showing an example of a functional configuration of a mammography apparatus and a console.

FIG. 6 shows an example of a functional configuration of the mammography apparatus 10 and the console 20. As shown in FIG. 6, in the mammography apparatus 10, the above-described controller 40 (see FIG. 2) functions as a radiography control unit 60 that controls the radiation source 15 and the radiation detector 19 to perform radiography. In the console 20, the above-described controller 50 (see FIG. 2) functions as a height information derivation unit 61 that derives the height information HI based on the visible light image PV and an imaging condition determination unit 62 that determines imaging conditions for radiography.

The radiography control unit 60 controls tube voltage and tube current of the radiation tube 15A (see FIG. 1) included in the radiation source 15 and irradiation time of the radiation R based on the imaging conditions determined by the imaging condition determination unit 62. The exposure dose of the breast as an imaging target is determined by the tube voltage, tube current, and irradiation time. In addition, the radiography control unit 60 controls the camera 30 to perform imaging in a case of pre-imaging with radiation.

The height information derivation unit 61 derives the height information HI based on the visible light image PV captured by the camera 30. Specifically, the height information derivation unit 61 derives the height information HI based on a rate of change in the length of the marker image MI according to the height H of the compression plate. The imaging condition determination unit 62 determines imaging conditions for performing main imaging based on the height information HI derived by the height information derivation unit 61 and a pre-captured image PX obtained by the pre-imaging. The pre-imaging is radiography performed at a low dose before the main imaging in order to determine the imaging conditions.

Figure 7:
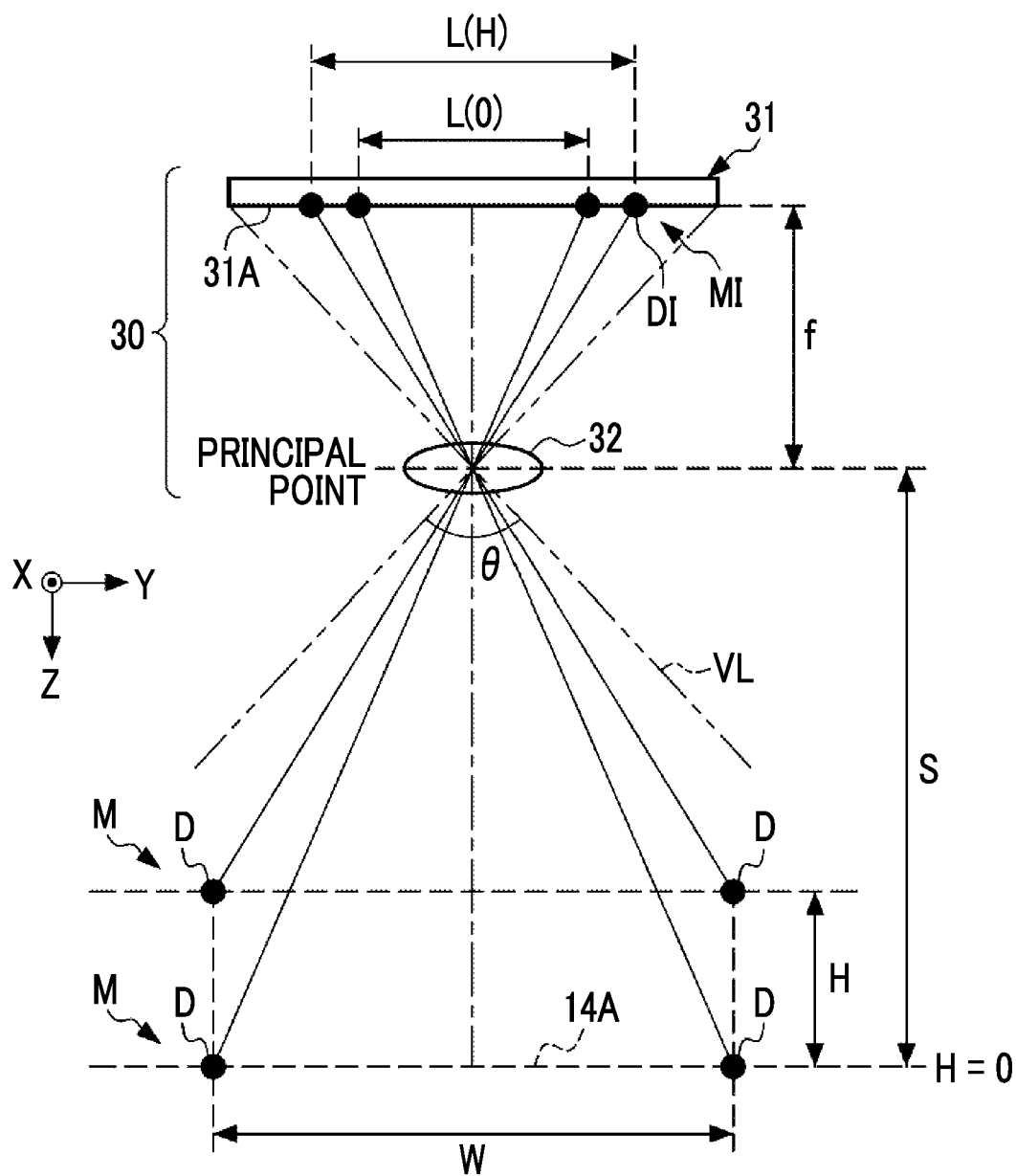
FIG. 7 is a diagram showing an example of processing of deriving height information.

FIG. 7 shows an example of processing of deriving the height information HI via the height information derivation unit 61. The camera 30 includes an imaging element 31 and a lens 32. The imaging element 31 is a two-dimensional image sensor such as a complementary metal oxide semiconductor (CMOS) type image sensor. The lens 32 is composed of one or a plurality of optical lenses. The imaging element 31 generates a visible light image PV by photoelectrically converting an optical image of the visible light VL formed on an imaging surface 31A by the lens 32.

In FIG. 7, f represents the focal length of the camera 30, and S represents the distance from the camera 30 to the exposure table 14. More specifically, f is the distance from the principal point of the lens 32 to the imaging surface 31A of the imaging element 31, and S is the distance from the principal point of the lens 32 to the exposure surface 14A of the exposure table 14. In FIG. 7, for simplification of the description, the thickness of the compression plate 16 is set to 0, and the marker M is shown at a position corresponding to the height H of the compression plate 16.

As shown in FIG. 7, even though the height H of the compression plate 16 changes, the interval W between the dots D included in the marker M does not change and is constant. From this, the following relational expressions (1) and (2) are obtained geometrically.

$$L(0)/f = W/S \quad (1)$$

$$L(H)/f = W/(S-H) \quad (2)$$

By arranging the relational expressions (1) and (2), the following relational expression (3) is obtained.

$$H = S(1 - L(0)/L(H)) \quad (3)$$

The height information derivation unit 61 obtains the interval L(H) between each of the dot images DI reflected in the visible light image PV and the adjacent dot image DI, and substitutes the obtained interval L(H) for the relational expression (3), thereby deriving the height information HI that is the two-dimensional distribution of the height H. Note that L(0) is the interval between the dot images DI obtained by imaging the marker M via the camera 30 in a state in which H=0. The distance S is a design value. The height information derivation unit 61 holds the values of the interval L(0) and the distance S in advance.

The height information derivation unit 61 may derive the height information HI by referring to a look up table (LUT) in which the relationship between the height H and the interval L(H) represented by the relational expression (3) is recorded.

In addition, in order to improve the measurement accuracy of the interval L(H) based on the visible light image PV, it is necessary to accurately obtain the center position of the dot image DI. In the present embodiment, since the dot D is circular, in a case where the compression plate 16 is inclined or deflected, the dot image DI has a shape close to an ellipse. Therefore, it is preferable that the height information derivation unit 61 measures the interval L(H) after obtaining the center position of the dot image DI via elliptical approximation of the dot image DI.

Figure 8:
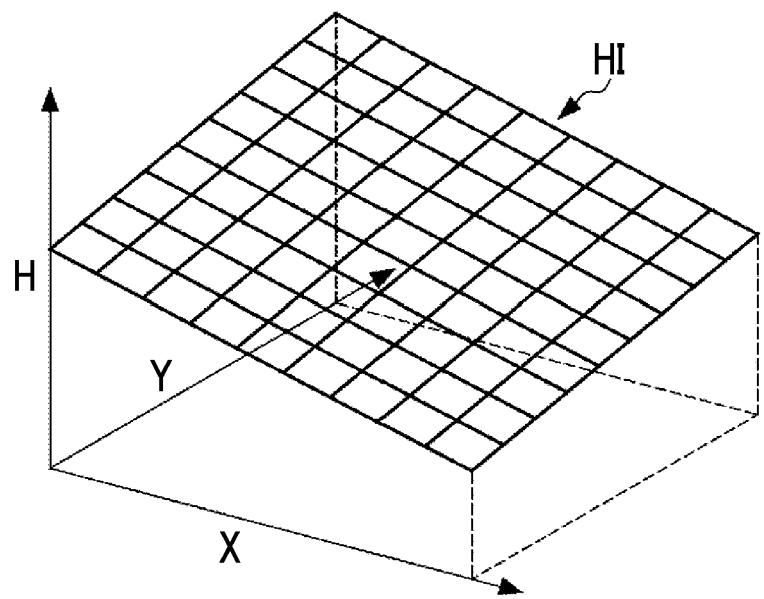
FIG. 8 is a diagram showing an example of the height information.
Figure 9:
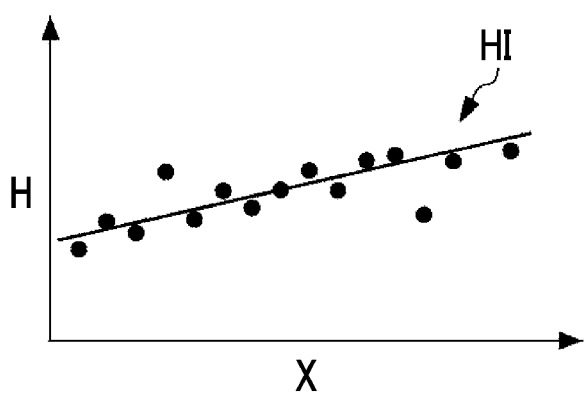
FIG. 9 is a diagram showing an example of smoothing processing.

FIG. 8 shows an example of the height information HI derived by the height information derivation unit 61. The height information HI is three-dimensional data representing the two-dimensional distribution of the height H. In a case of deriving the height information HI, the height information derivation unit 61 preferably performs smoothing processing and complementary processing on discrete data representing the height H of the compression plate 16 at a plurality of positions. FIG. 9 shows an example of smoothing processing. By performing the smoothing processing, the influence of noise that may occur in a case where the height H is derived can be removed. As the smoothing processing, filter processing such as moving average or Gaussian is used.

The thickness of the breast compressed during radiography (hereinafter, referred to as the compressed breast thickness) can be accurately detected by the height information HI derived by the height information derivation unit 61 while the breast is compressed by the compression plate 16.

Figure 10:
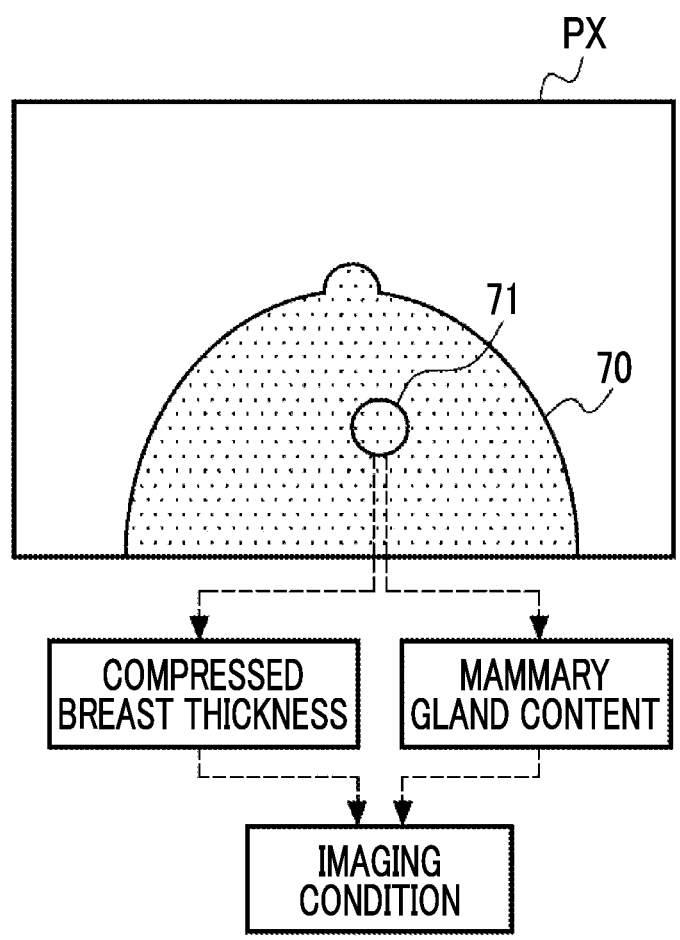
FIG. 10 is a diagram showing an example of processing of determining an imaging condition.

FIG. 10 shows an example of processing of determining the imaging conditions via the imaging condition determination unit 62. As shown in FIG. 10, the imaging condition determination unit 62 specifies, based on the pre-captured image PX, a region 71 in which the content of the mammary gland is equal to or higher than a certain value (hereinafter, referred to as a high-density mammary gland region) from a region 70 in which a breast image is reflected.

Specifically, the imaging condition determination unit 62 obtains the mammary gland content for each pixel of the pre-captured image PX based on the attenuation coefficient of the radiation R with respect to the mammary gland tissue and the adipose tissue. In a case of obtaining the mammary gland content for each pixel, the imaging condition determination unit 62 obtains the compressed breast thickness for each pixel based on the height information HI. The pixel value of the pre-captured image PX corresponds to the dose of the radiation R received from the radiation source 15. The imaging condition determination unit 62 calculates the mammary gland content based on the pixel value, the attenuation coefficient, and the compressed breast thickness. A method of calculating the mammary gland content is known, for example, in JP2020-000368A. According to the technique of the present disclosure, since the compressed breast thickness can be derived for each pixel based on the height information HI, the mammary gland content can be accurately calculated.

The imaging condition determination unit 62 obtains the compressed breast thickness and the mammary gland content of the high-density mammary gland region 71, and determines the imaging conditions based on the obtained compressed breast thickness and mammary gland content. The imaging conditions include tube voltage, tube current, and irradiation time.

In the high-density mammary gland region 71, since a lesion is often hidden in the mammary gland and is difficult to see, the imaging conditions are preferably set to the optimum values for the high-density mammary gland region 71. According to the technique of the present disclosure, since the compressed breast thickness in the high-density mammary gland region 71 can be accurately derived and the mammary gland content can be accurately derived, the optimum imaging conditions can be accurately determined.

Figure 11:
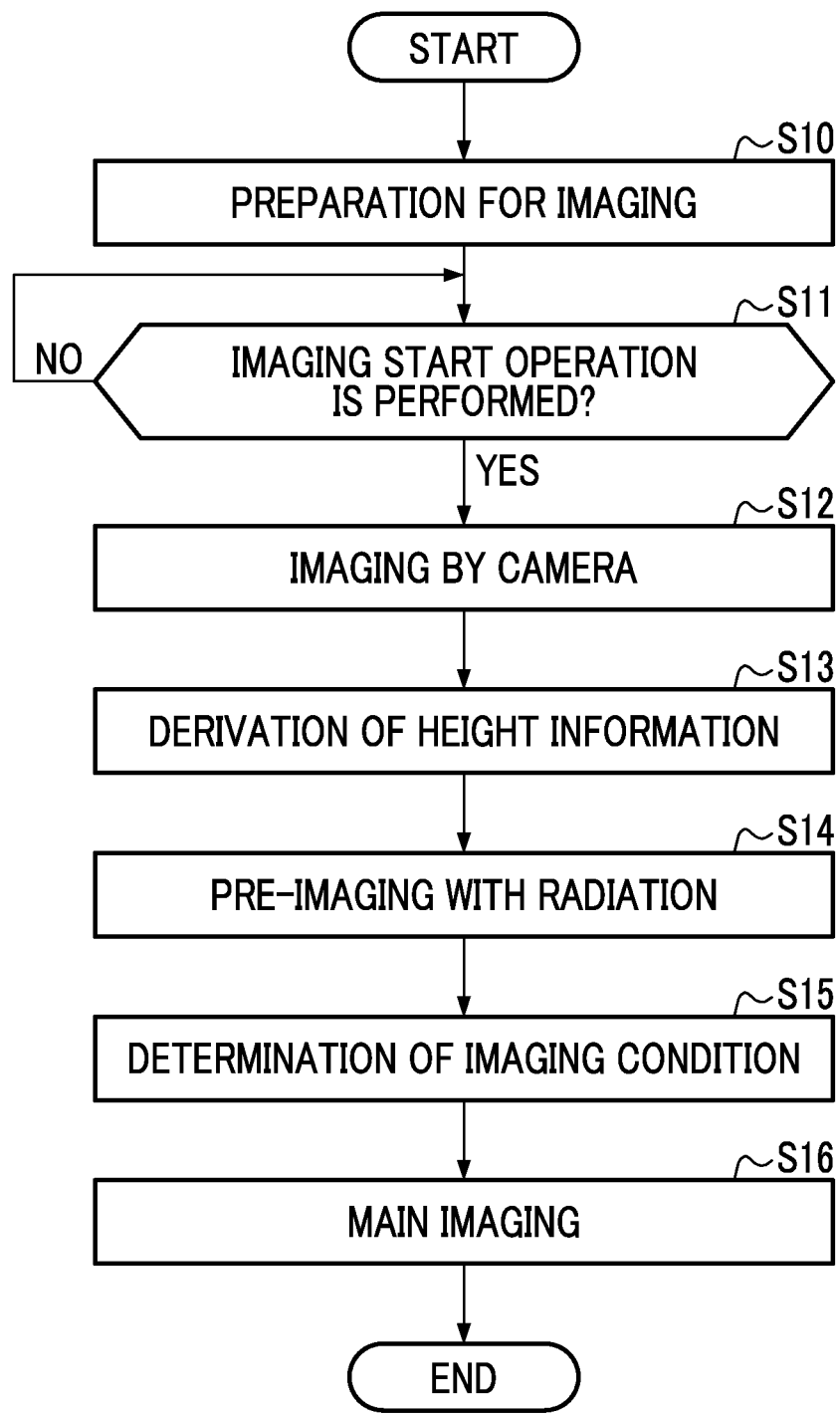
FIG. 11 is a flowchart showing an example of an operation of the radiographic system.
Figure 12:
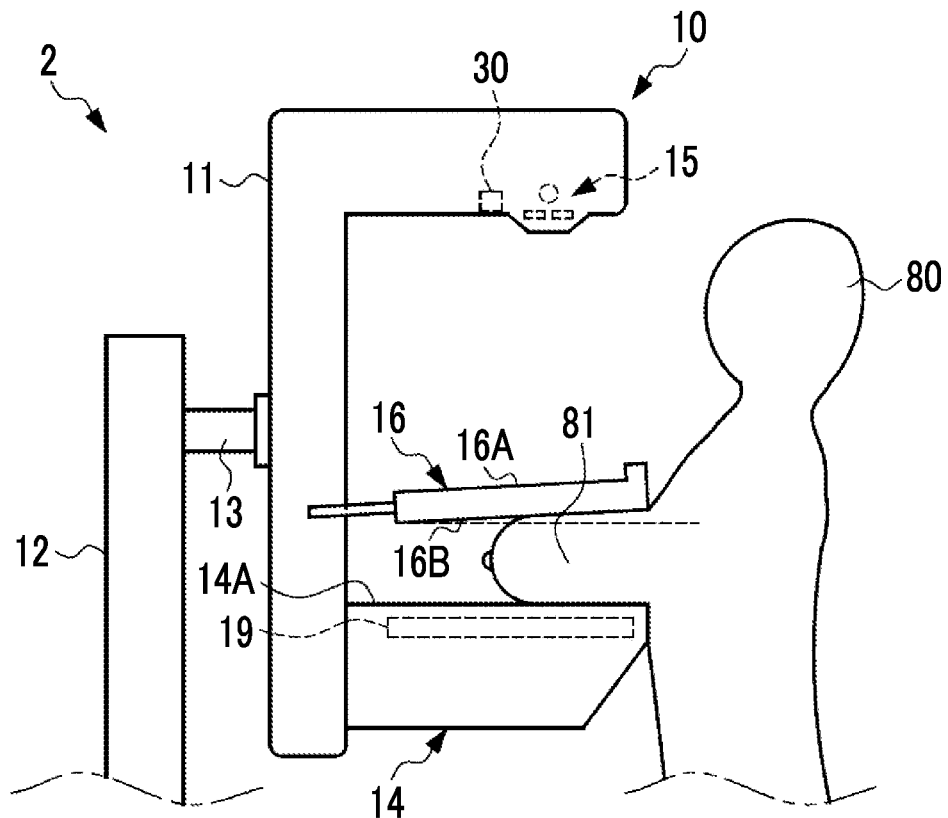
FIG. 12 is a diagram showing an example of a state in which a breast is compressed by the compression plate.

Next, the operation of the above configuration will be described with reference to a flowchart shown in FIG. 11. First, for example, the radiological technician sets the imaging method and the pre-imaging conditions by operating the operation unit 57 (see FIG. 2) of the console 20 in preparation for imaging (step S10). In addition, in step S10, as shown in FIG. 12, the radiological technician positions a breast 81 of a subject 80 placed on the exposure table 14 of the mammography apparatus 10 and then operates the operation panel 43 to compress the breast 81 via the compression plate 16. In this case, the compression plate 16 may be inclined or deflected.

Next, the radiography control unit 60 (see FIG. 6) determines whether or not the radiological technician has performed the imaging start operation using the operation panel 43 (step S11). In a case where it is determined that the imaging start operation has been performed (step S11: YES), the radiography control unit 60 causes the camera 30 to capture the visible light image PV including the marker M formed on the compression plate 16 (step S12). The visible light image PV captured by the camera 30 is transmitted to the console 20.

In the console 20, the height information HI is derived by the height information derivation unit 61 based on the visible light image PV (step S13).

In the mammography apparatus 10, the radiography control unit 60 controls the radiation source 15 and the radiation detector 19 to execute the pre-imaging (step S14). The pre-captured image PX generated by the radiation detector 19 is transmitted to the console 20.

In the console 20, the imaging condition determination unit 62 determines the imaging conditions based on the height information HI and the pre-captured image PX (step S15). The imaging conditions determined by the imaging condition determination unit 62 are transmitted to the mammography apparatus 10.

In the mammography apparatus 10, the radiography control unit 60 controls the radiation source 15 and the radiation detector 19 based on the imaging conditions received from the console 20 to execute the main imaging (main imaging with radiation) (step S16). The radiation image generated by the radiation detector 19 in the main imaging is transmitted to the console 20 and is displayed on the display unit 21.

As described above, according to the technique of the present disclosure, the height information derivation unit 61 derives the height information HI of the compression plate 16 based on the marker image MI indicating the marker M having the two-dimensional pattern reflected in the visible light image PV. As a result, the thickness of the breast can be accurately measured in consideration of the influence of the inclination or deflection of the compression plate 16.

Modification Examples

Next, various modification examples of the above embodiment will be described.

In the above embodiment, although the marker M has a dot shape consisting of a plurality of dots D, the marker M need only be a two-dimensional pattern whose length can be measured in at least two directions. The two-dimensional pattern of the marker M can be modified in various ways.

Figure 13:
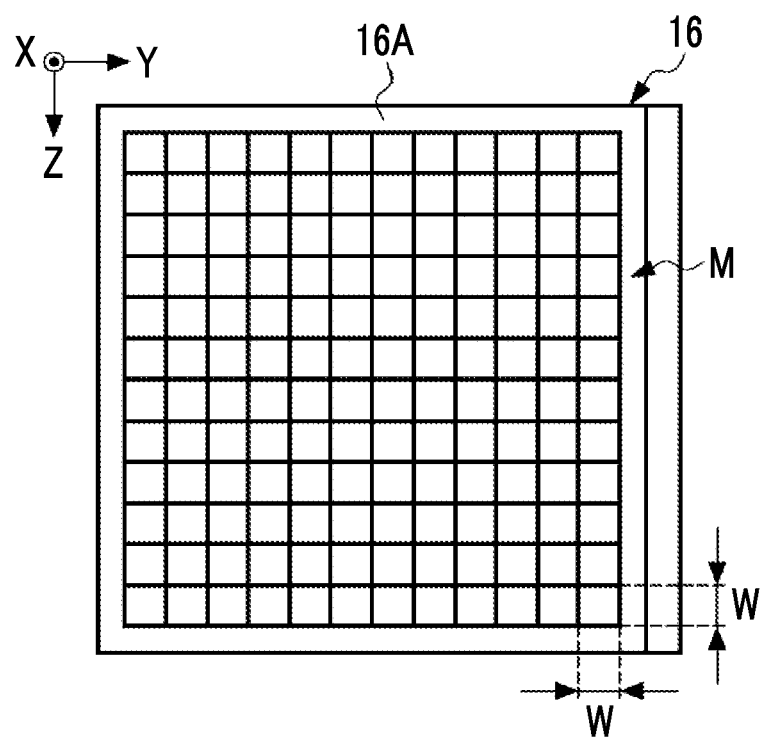
FIG. 13 is a diagram showing a first modification example of the marker.
Figure 14:
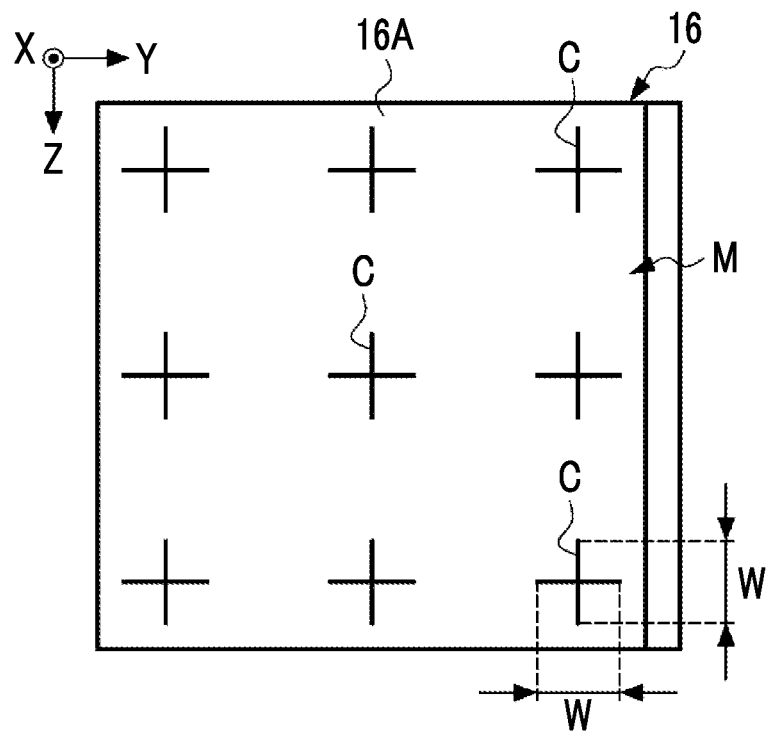
FIG. 14 is a diagram showing a second modification example of the marker.
Figure 15:
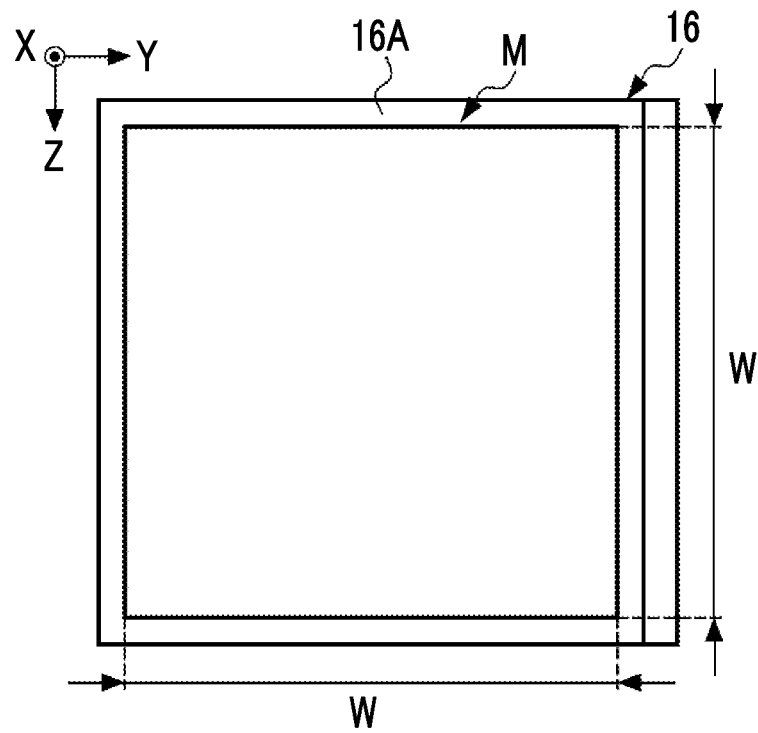
FIG. 15 is a diagram showing a third modification example of the marker.

FIGS. 13 to 15 show modification examples of the marker M. FIG. 13 is an example in which the two-dimensional pattern constituting the marker M is formed in a lattice shape. In the present example, for example, measurement need only be performed by setting the lattice interval in the X-axis direction and the Y-axis direction to W and the length of the marker image MI corresponding to the lattice interval W in the visible light image PV to L(H).

FIG. 14 is an example in which the two-dimensional pattern constituting the marker M is formed in a cross shape. The marker M includes a plurality of cross shapes C. In the present example, for example, measurement need only be performed by setting the length of the cross shape C in the X-axis direction and the Y-axis direction to W and the length of the marker image MI corresponding to the length W in the visible light image PV to L(H). W is not limited to the length of the cross shape C, and the distance between the two cross shapes C may be set to W.

FIG. 15 is an example in which the two-dimensional pattern constituting the marker M is formed in a frame shape. In the present example, for example, measurement need only be performed by setting the length of the side of the frame in the X-axis direction and the Y-axis direction to W and the length of the marker image MI corresponding to the length W in the visible light image PV to L(H). In the present example, since most of the marker M is located outside the breast, the marker M does not have to have a radiation-transmitting property. That is, the marker M may be formed of a material having radiation absorbency.

In the examples shown in FIGS. 14 and 15, since there are few positions at which the height H is measured in the compression plate 16, it is preferable to generate the height information HI for the entire surface of the compression plate 16 by performing the complementary processing.

In the above embodiment, the marker M is formed on the upper surface 16A of the compression plate 16, but in a case where the compression plate 16 is transparent, the marker M may be formed on the lower surface 16B of the compression plate 16. In addition, without forming the marker by printing or attaching a member, an edge portion of an outer periphery of the compression plate 16 may be regarded as a marker, and the height information HI may be derived based on the length of the edge portion of the compression plate 16 reflected in the visible light image PV.

In the above embodiment, the accuracy of the mammary gland content is improved by using the height information HI to calculate the mammary gland content. Further, the height information HI can be applied to energy subtraction processing for generating an energy subtraction image. The energy subtraction is a method of acquiring an image in which a specific structure is extracted by multiplying one of two radiation images obtained by irradiating a subject with two types of radiation having different energy distributions by an appropriate weight coefficient and then performing subtraction therebetween (see, for example, JP6667462B).

According to JP6667462B, the weight coefficient is determined based on a radiation absorption coefficient of the mammary gland tissue and the adipose tissue. The radiation absorption coefficient depends on the energy of the radiation, the compressed breast thickness, and the mammary gland content. Therefore, by accurately deriving the compressed breast thickness and the mammary gland content based on the height information HI, the separation accuracy of the substance (mammary gland tissue and adipose tissue) by the energy subtraction processing is improved. As a result, a high-quality energy subtraction image in which the mammary gland tissue is accurately extracted is generated.

The height information HI can also be applied to composite two-dimensional image generation processing of generating a composite two-dimensional image based on a plurality of tomographic images generated in tomosynthesis imaging. In the tomosynthesis imaging, a three-dimensional image consisting of a plurality of tomographic images is generated by reconstructing a plurality of projection images obtained by irradiating a subject with radiation from a radiation source at a plurality of radiation source positions. The composite two-dimensional image generation processing generates a composite two-dimensional image corresponding to a projection image by combining a plurality of tomographic images.

Figure 16:
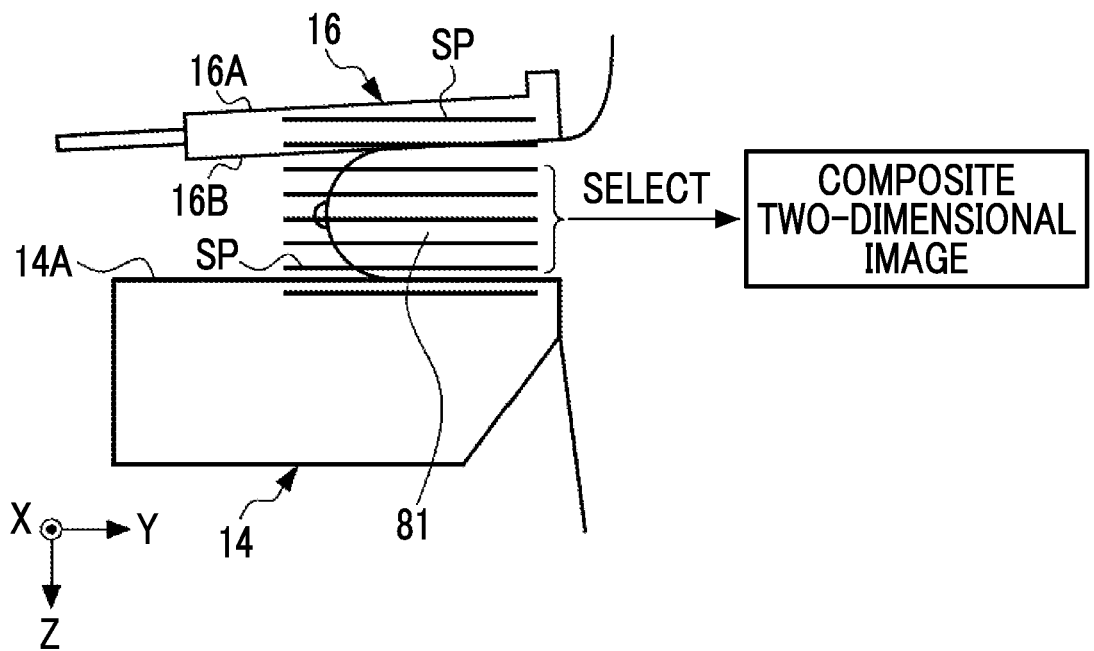
FIG. 16 is a diagram showing an example of generating a composite two-dimensional image based on a plurality of tomographic images.

In the tomosynthesis imaging, as shown in FIG. 16 as an example, a tomographic image SP is additionally generated in the vertical direction (Z-axis direction) so as to include the range of the breast 81 as an imaging target. That is, a part of a plurality of the tomographic images SP intersects the compression plate 16 or the exposure table 14. In a case where all of these tomographic images SP are selected and combined, the image quality of the breast reflected in the composite two-dimensional image is degraded. In particular, in a case where the compression plate 16 is inclined or deflected, the probability of selecting the tomographic image SP intersecting the compression plate 16 increases. With respect to this, by using the height information HI, the tomographic image SP intersecting only the breast 81 can be selected accurately. As a result, the image quality of the breast reflected in the composite two-dimensional image is improved.

Figure 17:
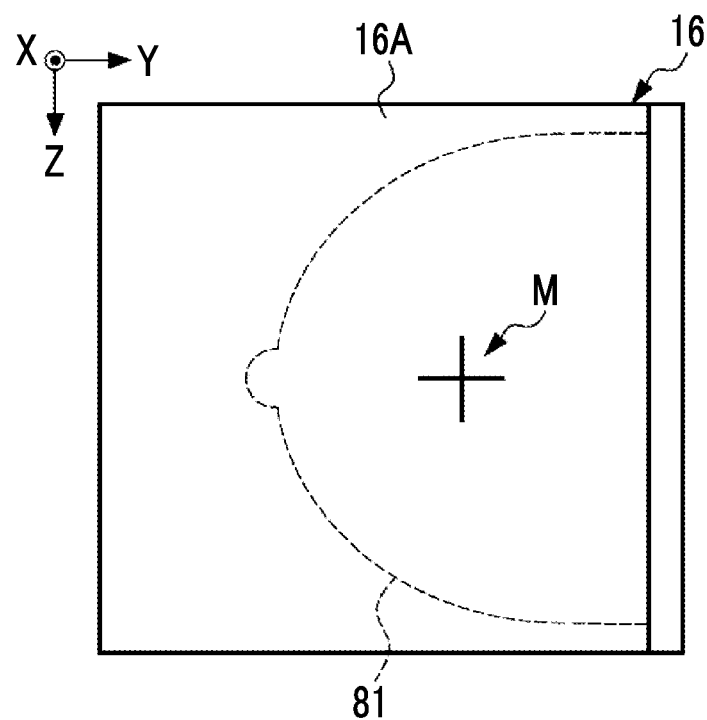
FIG. 17 is a diagram showing another modification example of the marker.

In the above embodiment and modification examples, the marker M having a two-dimensional pattern is formed on the compression plate 16, but one marker M having a predetermined shape may be formed on the compression plate 16. As an example, as shown in FIG. 17, in the compression plate 16, the marker M is disposed at a position overlapping the breast 81 placed on the exposure table 14. In the present example, the marker M has a cross shape. Based on the marker image reflected in the visible light image PV, the height of the compression plate 16 (that is, the compressed breast thickness) at the position where the marker M is disposed can be obtained.

In the present example, it is preferable that the marker M has a radiation-transmitting property. In the present example, the marker M is formed of a material having a radiation-transmitting property so as not to be reflected in the radiation image. The radiation transmittance of the marker M is not limited to 100% and may be less than 100%. The radiation transmittance of the marker M need only be such that it is not visible in the radiation image. In addition, the radiation transmittance of the marker M need only be substantially the same as the radiation transmittance of the compression plate 16. In a case where the radiation transmittance of the marker M is substantially the same as that of the compression plate 16, the image of the marker M is not visible in the radiation image even though the radiation transmittance is less than 100%.

From the above description, the techniques described in the following appendix claims 1 to 4 can be grasped.

APPENDIX 1

A radiographic system comprising:
an exposure table on which a breast of a subject is placed;
a compression plate that compresses the breast placed on the exposure table;
a marker having a radiation-transmitting property provided on the compression plate;
a radiation source that irradiates the compressed breast with radiation;
a camera that captures a visible light image including the marker; and
a processor that derives height information of the compression plate with respect to the exposure table based on a marker image showing the marker reflected in the visible light image.

APPENDIX 2

A radiographic apparatus comprising:
an exposure table on which a breast of a subject is placed;
a compression plate that compresses the breast placed on the exposure table;
a marker having a radiation-transmitting property provided on the compression plate;
a radiation source that irradiates the compressed breast with radiation; and
a camera that captures a visible light image including the marker.

APPENDIX 3

An information processing apparatus that is connected to a radiographic apparatus including an exposure table on which a breast of a subject is placed, a compression plate that compresses the breast placed on the exposure table, a marker having a radiation-transmitting property provided on the compression plate, a radiation source that irradiates the compressed breast with radiation, and a camera that captures a visible light image including the marker, the information processing apparatus comprising:
a processor,
wherein the processor derives height information of the compression plate with respect to the exposure table based on a marker image showing the marker reflected in the visible light image.

APPENDIX 4

An information processing method of a radiographic apparatus including an exposure table on which a breast of a subject is placed, a compression plate that compresses the breast placed on the exposure table, a marker having a radiation-transmitting property provided on the compression plate, a radiation source that irradiates the compressed breast with radiation, and a camera that captures a visible light image including the marker, the information processing method comprising:
deriving height information of the compression plate with respect to the exposure table based on a marker image showing the marker reflected in the visible light image.

In the above embodiment, for example, the hardware structure of a processing unit that executes various kinds of processing, such as the radiography control unit 60, the height information derivation unit 61, and the imaging condition determination unit 62, is various processors as shown below.

Various processors include a CPU, a programmable logic device (PLD), a dedicated electric circuit, and the like. As is well-known, the CPU is a general-purpose processor that executes software (programs) and that functions as various processing units. The PLD is a processor whose circuit configuration can be changed after manufacturing, such as a field programmable gate array (FPGA). The dedicated electric circuit is a processor having a circuit configuration designed to be dedicated to execute specific processing, such as an application specific integrated circuit (ASIC).

One processing unit may be constituted by one of these various processors, or may be constituted by a combination of two or more processors of the same type or different types (for example, a combination of a plurality of FPGAs or a combination of a CPU and an FPGA). In addition, a plurality of processing units may be constituted by one processor. As an example in which the plurality of processing units are constituted by one processor, first, one processor is constituted by a combination of one or more CPUs and software, and this processor functions as the plurality of processing units. Second, as represented by a system on chip (SoC) or the like, a processor that realizes the functions of the entire system including the plurality of processing units by using one IC chip is used. As described above, the various processing units are constituted by using one or more of the above-described various processors as the hardware structure.

The hardware structure of these various processors is more specifically an electric circuit (circuitry) in which circuit elements such as semiconductor elements are combined.

The present invention is not limited to the above-described embodiment, and of course, various configurations can be adopted without departing from the scope of the present invention. In addition to the program, the present invention extends to a computer-readable storage medium that stores the program in a non-temporary manner.

What is claimed is:

1. A radiographic system comprising:
an exposure table on which a breast of a subject is placed;
a compression plate that compresses the breast placed on the exposure table;
a marker having a two-dimensional pattern provided on the compression plate;
a radiation source that irradiates the compressed breast with radiation;
a camera that captures a visible light image including the marker; and
a processor that derives height information of the compression plate with respect to the exposure table based on a marker image showing the marker reflected in the visible light image.

2. The radiographic system according to claim 1,
wherein the processor derives the height information based on a rate of change in a length of the marker image according to a height of the compression plate.

3. The radiographic system according to claim 2,
wherein in a case where a distance from the camera to the exposure table is S, and a length of the marker image in one direction in a case where the height of the compression plate with respect to the exposure table is H is L(H), the processor derives the height information based on a relational expression of $H=S\times(1-L(0)/L(H))$.

4. The radiographic system according to claim 1,
wherein the height information includes a height of the compression plate at a plurality of positions.

5. The radiographic system according to claim 1,
wherein the two-dimensional pattern is any one of a frame shape, a lattice shape, a dot shape, a cross shape, or a combination thereof.

6. The radiographic system according to claim 1,
wherein the marker has a color different from a color of the compression plate.

7. The radiographic system according to claim 1,
wherein the marker is formed by attaching a member to the compression plate.

8. The radiographic system according to claim 1,
wherein the marker has a radiation-transmitting property.

9. The radiographic system according to claim 8,
wherein at least a part of the marker is disposed at a position overlapping the breast.

10. The radiographic system according to claim 1,
wherein the camera is provided in a holding part that holds the radiation source.

11. The radiographic system according to claim 1,
wherein the exposure table, the compression plate, the marker, and the camera are provided in a radiographic apparatus, and
the processor is provided in an information processing apparatus connected to the radiographic apparatus.

12. A radiographic apparatus comprising:
an exposure table on which a breast of a subject is placed;
a compression plate that compresses the breast placed on the exposure table;
a marker having a two-dimensional pattern provided on the compression plate;
a radiation source that irradiates the compressed breast with radiation; and
a camera that captures a visible light image including the marker;
wherein a processor that is in communication with the radiographic apparatus derives height information of the compression plate with respect to the exposure table based on a marker image showing the marker reflected in the visible light image.

13. An information processing apparatus that is connected to a radiographic apparatus including an exposure table on which a breast of a subject is placed, a compression plate that compresses the breast placed on the exposure table, a marker having a two-dimensional pattern provided on the compression plate, a radiation source that irradiates the compressed breast with radiation, and a camera that captures a visible light image including the marker, the information processing apparatus comprising:
a processor,
wherein the processor derives height information of the compression plate with respect to the exposure table based on a marker image showing the marker reflected in the visible light image.

14. An information processing method of a radiographic apparatus including an exposure table on which a breast of a subject is placed, a compression plate that compresses the breast placed on the exposure table, a marker having a two-dimensional pattern provided on the compression plate, a radiation source that irradiates the compressed breast with radiation, and a camera that captures a visible light image including the marker, the information processing method comprising:
deriving height information of the compression plate with respect to the exposure table based on a marker image showing the marker reflected in the visible light image.

* * * * *